(12) United States Patent
Wagh et al.

(10) Patent No.: US 7,083,672 B2
(45) Date of Patent: Aug. 1, 2006

(54) METHOD AND PRODUCT FOR PHOSPHOSILICATE SLURRY FOR USE IN DENTISTRY AND RELATED BONE CEMENTS

(75) Inventors: Arun S. Wagh, Naperville, IL (US); Carolyn Primus, Bradenton, FL (US)

(73) Assignees: Dentsply International, Inc., York, PA (US); University of Chicago, Chicago, IL (US)

( * ) Notice: Subject to any disclaimer, the term of this patent is extended or adjusted under 35 U.S.C. 154(b) by 0 days.

(21) Appl. No.: 10/913,185

(22) Filed: Aug. 6, 2004

(65) Prior Publication Data

US 2005/0028705 A1 Feb. 10, 2005

Related U.S. Application Data

(60) Provisional application No. 60/493,958, filed on Aug. 8, 2003.

(51) Int. Cl.
*A61L 24/02* (2006.01)

(52) U.S. Cl. .................. 106/35; 106/690; 106/691; 424/601; 424/602; 623/23.56; 623/23.62; 623/23.61; 501/1; 501/111; 501/154

(58) Field of Classification Search .............. 501/1, 501/154, 111; 106/35, 690, 691; 623/23.56, 623/23.62, 23.61
See application file for complete search history.

(56) References Cited

U.S. PATENT DOCUMENTS

| | | | |
|---|---|---|---|
| 3,923,534 A * | 12/1975 | Cassidy | .................. 501/109 |
| 4,283,382 A | 8/1981 | Frank et al. | |
| 4,374,120 A | 2/1983 | Soini et al. | |
| 4,600,389 A | 7/1986 | Schwartz | |
| 4,814,011 A | 3/1989 | Kamohara et al. | |
| 4,909,847 A | 3/1990 | Ohi et al. | |
| 4,936,775 A | 6/1990 | Bennett | |
| 5,645,518 A | 7/1997 | Wagh et al. | |
| 5,830,815 A | 11/1998 | Wagh et al. | |
| 5,864,894 A | 2/1999 | Fedele | |
| 6,133,498 A | 10/2000 | Singh et al. | |
| 6,153,809 A | 11/2000 | Singh et al. | |
| 6,204,214 B1 | 3/2001 | Singh et al. | |
| 6,214,048 B1 * | 4/2001 | Ito et al. | .................. 623/16.11 |
| 6,231,767 B1 | 5/2001 | Krofchak et al. | |
| 6,263,348 B1 | 7/2001 | Kathrow et al. | |
| 6,291,378 B1 | 9/2001 | Evans et al. | |
| 6,387,980 B1 | 5/2002 | Lu et al. | |
| 6,399,848 B1 | 6/2002 | Rechichi | |

(Continued)

*Primary Examiner*—C. Melissa Koslow
(74) *Attorney, Agent, or Firm*—McNees Wallace & Nurick LLC

(57) ABSTRACT

The present invention is directed to magnesium phosphate ceramics and their methods of manufacture. The composition of the invention is produced by combining a mixture of a substantially dry powder component with a liquid component. The substantially dry powder component comprises a sparsely soluble oxide powder, an alkali metal phosphate powder, a sparsely soluble silicate powder, with the balance of the substantially dry powder component comprising at least one powder selected from the group consisting of bioactive powders, biocompatible powders, fluorescent powders, fluoride releasing powders, and radiopaque powders. The liquid component comprises a pH modifying agent, a monovalent alkali metal phosphate in aqueous solution, the balance of the liquid component being water. The use of calcined magnesium oxide as the oxide powder and hydroxylapatite as the bioactive powder produces a self-setting ceramic that is particularly suited for use in dental and orthopedic applications.

25 Claims, 4 Drawing Sheets

U.S. PATENT DOCUMENTS

| | | |
|---|---|---|
| 6,458,423 B1 | 10/2002 | Goodson |
| 6,498,119 B1 | 12/2002 | Wagh et al. |
| 6,518,212 B1 * | 2/2003 | Wagh et al. ................ 501/111 |
| 6,521,264 B1 * | 2/2003 | Lacout et al. ................ 424/602 |
| 6,533,821 B1 | 3/2003 | Lally |
| 6,551,396 B1 | 4/2003 | Pineda et al. |
| 6,569,263 B1 | 5/2003 | Brown et al. |
| 2003/0131759 A1 | 7/2003 | Francis et al. |

* cited by examiner

METHOD AND PRODUCT FOR PHOSPHOSILICATE SLURRY FOR USE IN DENTISTRY AND RELATED BONE CEMENTS

CROSS-REFERENCE TO RELATED APPLICATIONS

This application claims the benefit of U.S. Provisional Application No. 60/493,958 filed Aug. 8, 2003, which application is hereby incorporated by reference.

STATEMENT REGARDING FEDERALLY SPONSORED RESEARCH

This invention was made with government support under Contract W-31-109-ENG-38 awarded by the Department of Energy. The Government has certain rights in this invention.

FIELD OF THE INVENTION

The present invention is directed to a method and product for magnesium phosphate ceramics for use in dentistry and orthopedics as a bonding material and as a bone bonding material.

BACKGROUND OF THE INVENTION

A quick setting ceramic that can be mixed in much the same way as phosphate concrete was originally developed by Argonne National Laboratory for radioactive and hazardous waste stabilization. This product is commonly referred to as Ceramicrete and has two components, a powder component and an aqueous component that are mixed together prior to use. The final Ceramicrete product is a magnesium potassium phosphate set material. The applications for Ceramicrete have been extended further to production of structural materials and in the process phosphosilicate ceramic was developed. Recent developments in Ceramicrete technology have been disclosed in several issued patents, all of which have Arun S. Wagh, one of the inventors of the present invention, as either a sole inventor or a co-inventor, including U.S. Pat. No. 5,645,518 issued Jul. 8, 1997; U.S. Pat. No. 5,830,815, issued Nov. 3, 1998; U.S. Pat. No. 5,864,894, issued Dec. 8, 1998; U.S. Pat. No. 6,133,498, issued Oct. 17, 2000 issued Oct. 17, 2000; U.S. Pat. No. 6,153,809 issued Nov. 28, 2000; U.S. Pat. No. 6,204,214 B1, issued Mar. 20, 2001; U.S. Pat. No. 6,498,119 B2, issued Dec. 24, 2002; U.S. Pat. No. 6,518,212 B1, issued Feb. 11, 2003; and U.S. Pat. No. 6,569,263 B2, issued May 27, 2003, which are incorporated herein by reference.

One ceramic material that has had some success as a binding material for industrial applications and waste management is the Ceramicrete binder. Ceramicrete binders disclosed include compounds such as magnesium potassium phosphate ($MgKPO_4.6H_2O$). These Ceramicrete binders are considerably less porous than conventional materials, are not toxic or flammable, set at a controllable rate, and are a low cost alternative to polymer resins.

The final set Ceramicrete phosphosilicate material is substantially without porosity. The substantially porosity-free Ceramicrete is made possible when calcium silicate ($CaSiO_3$) is added to create an amorphous silico-phosphate phase, which forms between the more crystalline $MgKPO_4.6H_2O$. The final Ceramicrete phosphosilicate products have a compressive strength comparable to or greater than the compression strength exhibited by portland cement.

However, only biocompatible components can make up the binding materials used in dentistry and orthopedics. For example, zinc phosphate materials have been used as dental materials because they are dense, hard and also biocompatible. Zinc phosphate cements, however, are not strong and not adhesive to metal. For these reasons and higher cost than portland cement, zinc phosphate cements are not practical for use in construction or waste encapsulation projects as well. Zinc phosphate cements also do not contain calcium phosphates or hydroxylapatite, which are desirable elements for bone tissue growth.

None of the previous binding materials provide a high strength, low porosity, rapid setting, easily colored, bioactive chemical composition needed for use in the bio-material industries of dentistry and orthopedics.

The high strength and extremely low porosity of Ceramicrete are two properties that are important to the field of dental materials and bone cements. The basic Ceramicrete composition is biocompatible. However, Ceramicrete as it is currently designed lacks a number of characteristics that would permit it to be used in dental and orthopedics applications. These characteristics include quick-setting at room and body temperatures, a range of low to high viscosity of the paste prior to setting, bioactive, radiopaque, and good bonding with tooth and bone materials. In addition, Ceramicrete is not designed to be fluorescent, fluoride-releasing, radiopaque, or to be a good color match with natural dentition.

In addition, dental materials and bone cements should generally have low exothermic heat, since they are used on the human body, and dimensional stability, as such materials should not expand or change shape to any noticeable degree. In addition, the dry powers used should be fine-grained for a smooth texture and quick dissolution and reaction. The creation of a phosphosilicate material mixture that has a final phosphosilicate set material with such characteristics would require significant modifications to the original Ceramicrete formulations.

Significant advances in dental materials and orthopedic cements have been achieved through the development of novel compositions and methods. However, given the expectations for continuous improvements in the dental and medical fields, there is a continuing need for further improvements to methods and materials for bonding materials for dentistry and to bond bone to other pieces of bone and other ceramic or metallic restorative materials. Furthermore, the concept of bioactivity where a material introduced into the body, stimulates the body to respond with the formation of bone to heal a defect, is of increasing importance. The present invention fulfils this need and further provides related advantages.

SUMMARY OF THE INVENTION

The present invention provides novel improvements over known chemically bondable phosphosilicate compositions and a method for making such improvements to known chemically bondable phosphosilicate compositions. The present invention has two primary components, a powder component and a liquid component and is designed to be combined into a paste that can be used for various dental and orthopedic purposes. The paste of the present invention is designed to be used as a dental material within the mouth for the various purposes known in the art to which dental material is used. The paste of the present invention is also designed to be used as a general purpose bone cement in the field of orthopedics.

The phosphosilicate ceramic mix of the present invention comprises about 65 weight percent to about 85 weight percent of a powder component and about 15 weight percent to about 35 weight percent of a liquid component.

The powder component comprises about 5 weight percent to about 15 weight percent of a sparsely soluble powder selected from the group consisting of a sparsely soluble oxide powder, a sparsely soluble hydroxide powder, and combinations thereof, about 15 weight percent to about 45 weight percent metal phosphate powder wherein the metal is selected from the group consisting of alkali metals, alkaline earth metals, group III metals, and combinations thereof, and about 15 weight percent to about 35 weight percent of a sparsely soluble silicate powder. The balance of the powder is at least one powder selected from the group consisting of coloring powders, texturing powders, bioactive powders, biocompatible powders, fluorescent powders, fluoride releasing powders, and radiopaque powders. In, in a preferred embodiment 5 weight percent to about 25 weight percent of another powder is added that makes the material more suitable for use in the body, depending on the proposed indication for use of the material. This powder may be added for bioactivity, biocompatibility, fluorescence, fluoride release, or radiopacity. The powders are blended together.

The present invention also includes at least one additional powder component that permits the phosphosilicate material of the present invention to possess at least one characteristic that is beneficial to utilizing the material as a dental material and/or orthopedic bone cement. As is known in the art, it is helpful to have such materials possess a degree of radiopacity, which permits the material to show up when X-rays are taken of the area of the body to which the material has been applied, permitting a practitioner to detect the placement of the ceramic product. Such radiopacity may be accomplished through the use of an additional radiopaque powder element such as a non-hazardous heavy metal oxide or sulfate. If fluoride-containing compounds are included in the powder for a dental material, the fluorides can provide a very slow leaching of fluorine into the oral environment potentially reducing carries. In the present invention, fluorides can readily be incorporated into the ceramic paste without significantly altering the setting of the material. Fluorine atoms have a very slow leaching rate from the material of the present invention.

The liquid component comprises up to about 20 weight percent of a pH modifying acid, such as phosphoric acids and dihydrogen phosphates of di- or tr-valent metals, including, but not limited to ortho phosphoric acid, $Ca(H_2PO_4)_2 \cdot H_2O$, $Fe(H_2PO_4)_2 \cdot nH_2O$, $Zn(H_2PO_4)_2 \cdot nH_2O$, $Al(H_2PO_4)_3 \cdot H_2O$, $H_3PO_4$ (phosphoric acid), up to about 60 weight percent of powders of these acid phosphates, including, but not limited to $MgH_2PO_4 \cdot H_2O$, in solution, and the balance of the liquid component is water. No externally applied heat is required to effectuate the reaction that forms the material of the present invention.

The present invention may also include optional materials for fluorescence when the material is exposed to ultraviolet light. While the potassium in the material makes the material naturally slightly fluorescent, additional fluorescent materials, such as, for example, fluorescent glasses containing lanthanides, or lanthanide containing fluorides are readily incorporated into the material.

The phosphosilicate material of the present invention may also include an additional optional material for altering the texture and color of the material. As is known in the art, texture and color are often important for dental materials, as very often the materials are visible to the naked eye once applied to oral cavity. The color and texture of the dental material should blend in with the color and texture of the surrounding tissue and teeth. To create a material that is esthetically pleasing and to match natural dentition, a non-hazardous metal oxide or metal hydroxide may be added to the powder component in order to provide coloring or surface gloss.

Dental materials and bone cements are often applied to areas where the long-term presence of such materials often require a degree of bioactivity so that the material can easily interact with surrounding biological tissue. Additional optional known bioactive materials, such as hydroxylapatite ($Ca_5(PO_4)_3OH$), may be added to the powder component and/or synthesized during the chemical reaction that forms the set phosphosilicate material to increase the bioactivity of the set material. During setting of the material, the materials in the present invention will react with tooth and/or bone material to form a chemical bond, as opposed to a Van der Waals or potentially weaker mechanical bond. Depending on the bioactive and/or biocompatible material used for the present invention, components of the material can be resorbed into the body and/or may permit tissue regeneration in the body.

Prior to application in the mouth and/or bone, the powder component is blended together and mixed with the liquid component acidic aqueous solution to form a paste. Once the paste has a consistency sufficient to use the paste as a dental paste or bone cement, the paste is applied to either the mouth and/or bone in the same manner as dental materials and/or orthopedic cement known in the art. Once the paste of the present invention is properly applied, as known in art, the material is allowed to set.

For smooth consistency of the paste and homogeneity of the set material, the powders should be ground to about 400 mesh or finer, which helps to reduce the mixing time and working time, as smaller particles permit the chemical reaction of the present invention to proceed more rapidly. A fixed weight of fine powders has a greater surface area than the same weight of larger powders. Increasing the surface area of the reactants generally increases the speed with which a reaction achieves equilibrium. In addition, the use of fine powders permits the creation of a more homogenous paste. This also makes the paste feel smooth to the practitioner while mixing, and enables the material to penetrate the finest pores in bone and teeth.

In addition to reducing the particle size of the powders, reducing the pH of the mixed paste will reduce the mixing time and working time of the present invention. Standard phosphosilicate material paste has a pH of below 7.0 when first mixed together. By further reducing the pH of the present invention through the addition of the pH modifier, the mixing time and working time can be reduced as desired by the practitioner. Ideally, pH should remain above about 3.0 to avoid deleterious affects on surrounding body tissues.

The material of the present invention can readily be mixed on the small scale necessary for its use in dentistry and/or orthopedics. Acceleration of mixing time can also be accomplished through the use of an ultrasonic dental probe and/or ultrasonic bath. The use of such ultrasonic energy allows rapid dissolution of the powders that will speed up the chemical reactions in the paste.

For the present invention the term "mixing time" is a measure of how quickly the powder and liquid can be mixed together to form a paste of sufficient consistency and chemical composition that it can be applied to the oral cavity or bone before setting begins into the final phosphosilicate set material. For the present invention, the term "working tim"

is a measure of how long the dental or orthopedic practitioner has to work with the mixed ceramic paste before the paste has set to the point where it is no longer adequately malleable. The mixing time of the paste of the present invention is about 3 minutes or less, which is an appropriate mixing time for dental and orthopedic materials. The working time of the present invention is about 5 minute to about 15 minutes after the material has been mixed. For dental materials and bone cements, mixing time should be about 3 minutes or less and working time should be about 5 minutes to about 15 minutes, which is the mixing time and working time of the present invention. If the working time is shorter than about 5 minutes, then the practitioner does not have sufficient time to work with the material. If the working time is longer than about 15 minutes, then the practitioner has to spend more time than necessary dealing to finish the procedure which is inconvenient for the practitioner and the patient. Furthermore, during setting, the material can be accidentally dispersed from its intended location and slippage of bonded elements could result.

The end product produced by mixing the powder component and the liquid component has crystalline and non-crystalline phosphates of Mg, Ca, and other optional metal phosphates.

An advantage of the present invention is that the high strength of known phosphosilicate materials can be utilized in the mouth and on bone and related materials to provide a strong, long-lasting bond.

A further advantage of the present invention is that the pH of the paste can be reduced, which, combined with the small particle size of the powders, accelerates mixing time and working time.

Another advantage of the present invention is that biologically compatible and/or bioactive materials can be added to the phosphosilicate materials, which permits resorption into the body and/or promotes the growth of new tissue.

Another advantage of the present invention is that radiopaque materials can be added to the material to allow a practitioner to detect the placement of the set material product using X-rays.

Another advantage of the present invention is that fluorescent materials can be added to the material to match the natural fluorescence of teeth in ultraviolet light.

Another advantage of the present invention is that powders can be added to the material to enhance the texture and/or color of the phosphosilicate material for use in dental applications.

Still another advantage of the present invention is that fluorine can be added to the dental material, potentially reducing the number of caries in the area of the dental material.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
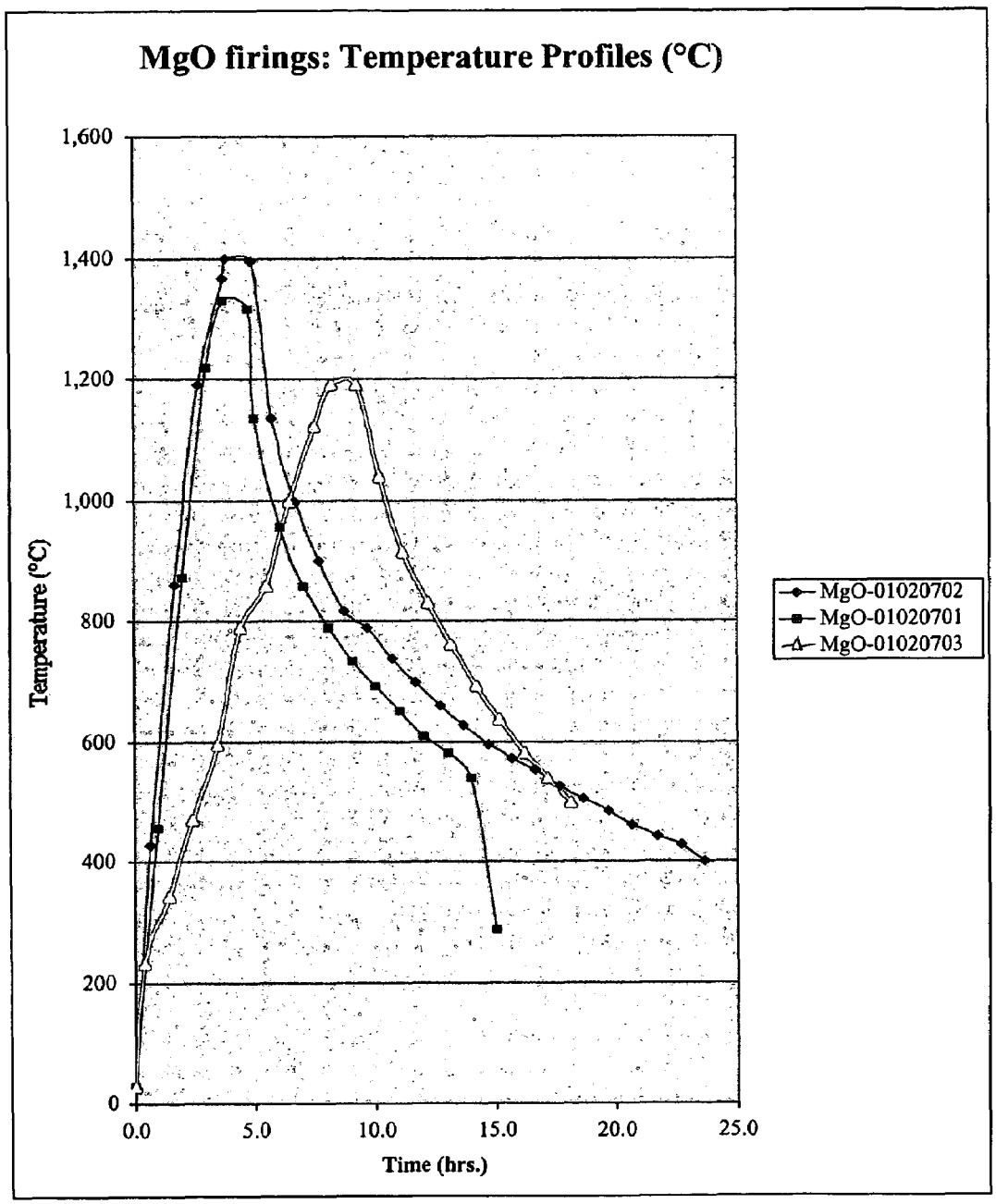
FIG. 1 is a graph of the time and temperature of the calcining of the MgO used to create the experimental samples of various embodiment of the present invention.

The present invention is a novel composition for creating a fast-setting phosphosilicate material with aqueous and powder components for use as either a dental material or orthopedic cement. The slurry composition of the present invention has two primary components, a substantially dry powder and an aqueous solution. The phosphosilicate ceramic mix of the present invention comprises about 65 weight percent to about 85 weight percent of a powder component and about 15 weight percent to about 35 weight percent of an aqueous component. The reaction between the powder and the aqueous solution is primarily an acid-base reaction that forms crystalline and amorphous products. The final set material comprises oxides and phosphates as well as hydrophosphates that provide optional radiopacity, color, fluorescence, bioactivity, biocompatibility, and chemically bond the material to dental and/or bone substrates(s).

The material of the present invention can be used as a root canal sealer, a root canal obturation material, a root canal repair material, a pulp-capping material, a temporary cement, temporary restorative material, a cement for a prosthodontic crown—either metal or ceramic, cement for implants, cement for avulsed teeth, dental ridge augmentation material, periodontal defect filler, bone defect filler such as after an apicoectomy, bracket or band cement for orthodontics, pulp-capping material, coronal capping material for endodontics, cement for artificial joints and bone stabilizing cement. Its applications are not limited to these uses, but may be used in any application that requires a material in the fields of dentistry and/or orthopedics.

The powder component comprises about 5 weight percent to about 15 weight percent of a sparsely soluble powder selected from the group consisting of a sparsely soluble oxide powder, a sparsely soluble hydroxide powder, and combinations thereof, about 15 weight percent to about 45 weight percent monovalent alkali metal phosphate powder, and about 15 weight percent to about 35 weight percent of a sparsely soluble silicate powder. The balance of the powder component comprises at least one powder selected from the group consisting of bioactive powders, biocompatible powders, fluorescent powders, fluoride-releasing powders, and radiopaque powders. In one embodiment the sparsely soluble powder, metal phosphate powder, and sparsely soluble silicate powder each have a particle size of less than 20 μm. In another embodiment, the sparsely soluble silicate powder is at least one of $CaSiO_3$, $MgSiO_3$, $BaSiO_3$, and $Mg_3Si_2O_5(OH)_4$ and has a particle size of no greater than about 100 μm. In yet another embodiment, the sparsely soluble silicate powder is at least one of $CaSiO_3$, $MgSiO_3$, $BaSiO_3$, and $Mg_3Si_2O_5(OH)_4$ and has a particle size of between about 1 μm and about 20 μm.

In a preferred embodiment, the total weight percent of the powder component comprising the sparsely soluble powder selected from the group consisting of a sparsely soluble powder, a sparsely soluble hydroxide powder, and combinations thereof, the monovalent alkali metal phosphate powder, and the sparsely soluble silicate powder is about 75 weight percent and the balance of the powder component comprises at least one powder selected from the group consisting of bioactive powders, biocompatible powders, fluorescent powders, fluoride-releasing powders, and radiopaque powders The sparsely soluble powder may include any oxide and/or hydroxide powder used in Ceramicrete binder known in the art, including, but not limited to, magnesium oxide (MgO), calcium oxide (CaO), zirconium oxide ($ZrO_2$), iron oxide (FeO and/or $Fe_3O_4$), lanthanum oxide ($La_2O_3$), and combinations thereof. In a preferred embodiment, MgO is the sparsely soluble oxide powder. In an alternative embodiment, the sparsely soluble powder is a mixture of MgO and CaO, $Al(OH)_3$, $Zr(OH)_4$, and combinations thereof.

The particle size of the present invention is important for the smooth consistency of the paste and homogeneity of the material. In previous versions of Ceramicrete, the powders were ground to finer than about 200 mesh. In the present invention, the particle size of the MgO and $KH_2PO_4$ should be less than about 400 mesh. In particular, the use of fine particles size creates a final set material with a more homogenous microstructure, which means that the final set material has a surface that is smoother than the prior Ceramicrete does. Furthermore, the finer particle size allows for faster setting than is needed in waste disposal application where a large amount of material must be mixed and reacted. Various calcium silicate particle sizes may be used for different applications, provided that the maximum length in any dimension of calcium silicate powder, which has an elongated acicular structure, is not greater than about 100 µm. In a preferred embodiment the mean dimension in any length of calcium silicate powder is about 3 µm to about 10 µm. These finer powders create a working paste after mixing having a relatively low viscosity and a relatively smooth paste. Coarser powders creating a working paste having a higher viscosity and rougher paste and may be slightly stronger because of a high aspect ratio of the calcium silicate, needle-like, powder particles.

In one embodiment, at least one powder has a particle size of between about 5 µm and about 500 µm. In another embodiment, the sparsely soluble silicate powder has a particle size of no greater than about 100 µm. In another embodiment, the sparsely soluble oxide and/or hydroxide powder, metal phosphate powder, and sparsely soluble silicate powder each have a particle size of less than 20 µm. In another embodiment, the sparsely soluble silicate powder has a particle size of between about 1 µm to about 20 µm.

The monovalent alkali metal phosphate powder may include any Ceramicrete component powders known in the art, including, but not limited to $KH_2PO_4$ (potassium dihydrogen phosphate), $NaH_2PO_4$, and combinations thereof. In an alternative embodiment, divalent and trivalent metal phosphate powders such as, but not limited to $Mg(H_2PO_4)_2$ (magnesium dihydrogen phosphate) and $Al(H_2PO_4)_3$ (aluminum dihydrogen phosphate), may be used in the place of monovalent alkali metal phosphate powders. In another alternative embodiment, the metal phosphate powder may be selected from the group consisting of $NaH_2PO_4$, $KH_2PO_4$, $Mg(H_2PO_4)_2$, $Al(H_2PO_4)_3$, and combinations thereof. If $NaH_2PO_4$ is used, the molar ratio MgO to $NaH_2PO_4$ is preferably about 1:1. If $KH_2PO_4$ is used, the molar ratio of MgO to $KH_2PO_4$ is preferably about 1:1. If $Mg(H_2PO_4)_2$ is used, the molar ratio of MgO to $Mg(H_2PO_4)_2$ is about 2:1. if $Al(H_2PO_4)_3$ is used, the molar ratio of MgO to $Al(H_2PO_4)_3$ is about 3:1.

The sparsely soluble silicate powder can include $CaSiO_3$ (calcium meta-silicate, also known as wollastonite), $MgSiO_3$ (magnesium silicate, also known as talc), $BaSiO_3$ (barium silicate), $Mg_3Si_2O_5(OH)_4$ (chrysotile), and combinations thereof.

In addition, the powder component may comprise from about 0 weight percent to about 25 weight percent of a bioactive powder such as $Ca_5(PO_4)_3OH$ (hydroxylapatite). The particle size of the hydroxylapatite may be small and spherical (about 16 µm mean diameter), or the particles may be larger (up to about 500 µm) and acicular. Without wishing to be bound by theory, it is presumed that the more acicular hydroxylapatite may give added strength. Hydroxylapatite is a component that is useful in biomaterial applications as it is a strong, dense material that mimics natural bone composition and may stimulate the regeneration of tissues in the body. When hydroxylapatite forms on the surface of another product, tissue regeneration may occur. Human bones and teeth contain a high percentage of calcium phosphate compounds such as hydroxylapatite and other calcium phosphates. In an alternative embodiment, a precursor to hydroxylapatite, tetracalcium phosphate ($Ca_4(PO_4)_2O$) may be used as a powder component instead of using the hydroxylapatite itself. When the material sets, a calcium hydrophosphate is formed which may react in the body with the tetracalcium phosphate to form hydroxylapatite. In another alternative embodiment, both hydroxylapatite and tetracalcium phosphate may be used as powder components.

To allow the user to detect the placement of the set product using X-rays, it is necessary to modify the composition of the present invention to be more radiopaque. Such detection by X-rays is helpful to both dental and other medical practitioners to determine the areas of the body to which the X-rays have been applied. An optional powder component is additional radiopaque materials including a variety of heavy metal oxides, sulfates, and fluorides that are not hazardous. Typical examples include, but are not limited to bismuth oxide ($Bi_2O_3$), zinc oxide (ZnO), barium sulfate ($BaSO_4$) lanthanum oxide ($La_2O_3$), cerium oxide ($CeO_2$), terbium oxide, ytterbium oxide, neodymium oxide, zirconia ($ZrO_2$), strontia (SrO), tin oxide ($SnO_2$), and radiopaque glasses such as barium silicate, silico-alumino barium or strontium containing glasses. Radiopaque silicate glasses containing as barium or strontium are well known in the art and have been disclosed in U.S. Pat. No. 4,936,775, issued Jun. 26, 2003; and U.S. Pat. No. 6,387,980 B2 issued May 14, 2002, both of which have been assigned to Dentsply Research & Development Corp., and both of which are incorporated herein by reference. Such radiopaque glasses permit the composition of the present invention to be readily visible in x-rays of the mouth or other body parts. In a preferred embodiment the powder component comprises about 0 weight percent to about 25 weight percent of an radiopaque oxide selected from the group consisting of bismuth oxide, lanthanum oxide, cerium oxide, zirconia, strontia, tin oxide, barium sulfate, barium and/or strontium silicate-based glasses, and combinations thereof. In a more preferred embodiment the powder component comprises up to about 25 weight percent bismuth oxide as the optional heavy metal component.

In addition to hydroxylapatite, other materials that enhance the biological compatibility of the ceramic and the bioactivity of the ceramic can optionally be included in the powder component. One such material is PEPGEN-15®, a synthetic peptide-containing powder, which is a well-known proprietary synthetic compound that enhances cell binding with respect to collagen, disclosed in U.S. Pat. No. 6,263,348, issued Jul. 31, 2001, and which is incorporated herein by reference. Another such material is BIOGLASS®, a calcium and phosphorous-containing glass, which is a well-known proprietary bone grafting material that aids in the regeneration of bone and periodontal tissue, as it is osteostimulative and resorbable. PEPGEN P-15® is a trademark of CeraMed Dental, L.L.C. of Lakewood, Colo. BIO-GLASS® is a trademark of the University of Florida of Gainesville, Fla. In a preferred embodiment, the powder composition comprises from about 0 weight percent to about 25 weight percent of a bioactive material selected from the group consisting of a synthetic compound that enhances cell binding with respect to collagen, a bone grafting material that aids in the regeneration of bone and periodontal tissue, and combinations thereof.

An additional material in the powder component can optionally be a non-hazardous material that is fluorescent under ultra-violet light. Such fluorescence makes a dental restorative material appear more like natural teeth, particularly when viewed in ultra-violet light. As the composition of the present invention contains potassium, is naturally slightly fluorescent under ultra-violet light. To augment this fluorescent appearance, up to about 25 weight percent fluorescent glasses containing lanthanide glasses and/or oxides containing lanthanides can be used in the composition of the present invention. Such glasses include, but are not limited to, cerium oxide, praseodymium oxide, terbium oxide, erbium oxide, ytterbium oxide, neodymium oxide, and combinations thereof. Glasses containing lanthanides are well known in the art and have been disclosed in U.S. Pat. No. 4,600,389, issued Jul. 15, 1986; U.S. Pat. No. 4,374,120, issued Feb. 15, 1983; and U.S. Pat. No. 4,283,382, issued Aug. 11, 1981, which are incorporated herein by reference. Such fluorescent glasses are often used in dental formulations in order to allow dental practitioners to improve the esthetics of the dental restorative material. The use of fluorescent glasses containing lanthanides in the present invention will enhance the naturalness of the material when used for a dental restorative material.

In addition to the above-mentioned optional supplemental materials in the powder component, fluorides can also be added to the composition of the present invention. Up to about 25 weight percent fluorescent glasses containing lanthanides can be used in the composition of the present invention. Such fluorides include, but are not limited to calcium fluoride, potassium fluoride, stannous fluoride, fluoride-releasing glasses, and combinations thereof. As known in the art, fluorides can provide a very slow leaching of fluorine into the oral environment potentially reducing caries. This advantage is available in the composition of the present invention because fluorides can be incorporated without altering the setting time of the present invention. Without wishing to be bound by theory, it is presumed that the fluorine atoms also have a very low leaching rate from the set product of the present invention.

The powder component of the present invention may optionally also include an additional material for altering the texture and color of the material. As is known in the art, texture and color are often important for dental materials, as very often the materials are visible to the naked eye once applied to oral cavity. The color and texture of the dental material should blend in with the color and texture of the surrounding tissue and teeth, or alternatively, should stand out from the underlying bone, teeth, and/or other tissue in order to aid the practitioner in the application of the material of the present invention. To create material that is esthetically pleasing and to match natural dentition, or to contrast with natural dentin, a non-hazardous metal oxide may be added to the powder component in order to provide coloring or surface gloss. In a preferred embodiment, the powder composition comprises up to about 25 weight percent of a color and/or texture altering material selected from the group consisting of $Al_2O_3$ (alumina for surface gloss), $Al(OH)_3$ (aluminum hydroxide for surface gloss), $Fe_3O_4$ (iron oxide for grey color), $Fe_2O_3$ (iron oxide for red color), $CeO_2$ (cerium oxide for white or tan color), $Bi_2O_3$ (bismuth oxide for yellow color), and combinations thereof. With the use of such additional coloring powders, the set material will be able to match the color, texture, and appearance with the host tooth or bones better than several commercial products available in the market.

In a preferred embodiment, the preselected powder composition component is blended together prior to mixing the powder component with the aqueous component.

In the present invention, the liquid component comprises, up to about 20 weight percent of a pH modifying acid, up to about 60 weight percent of a monovalent alkali metal phosphate powder in solution, the balance water. In one embodiment, a pH modifying agent comprises between about 5 percent by weight to about 15 percent by weight of the liguid component. While the pH modifying acid can be any suitable acid, ammonium phosphate ($NH_4H_2PO_4$) and phosphoric acid ($H_3PO_4$) are preferable. In a preferred embodiment, the pH modifying acid is $H_3PO_4$ comprising about 5 percent by weight to about 11 percent by weight of an aqueous solution. In a preferred embodiment the pH modifying acid is $H_3PO_4$ comprising about 11 percent by weight in an aqueous solution. Reducing the pH, which occurs with the use of $H_3PO_4$, will decrease the mixing and working time of the phosphosilicate paste of the present invention. Such a reduction in pH can also be useful for etching of teeth in certain applications, such as adhesion of a ceramic crown. However, a low pH could cause injury to the tooth in certain applications, such as pulp-capping. In a preferred embodiment, the monovalent alkali metal phosphate is $Mg(H_2PO_4).H_2O$ (magnesium dihydrogen phosphate hydrate). In a more preferred embodiment, the $Mg(H_2PO_4).H_2O$ is dissolved into the aqueous solution prior to mixing the liquid component with the powder component at about 50 percent by weight of the aqueous solution. The use of $Mg(H_2PO_4).H_2O$ does reduce both the mixing time and the working time of the phosphosilicate paste of the present invention. In all cases, once the material of the present invention is thoroughly mixed, the pH will go to about 7.

When the aqueous component is combined with the powder component, a paste of appropriate consistency will be able to be mixed in about 3 minutes or less. In a preferred embodiment, the mixing time is about or less than about 2 minutes. Bone cements may require a longer mixing time than dental cements. In an optional embodiment, such mixing is accomplished through the use of either an ultrasonic dental probe or an ultrasonic bath. The use of ultrasonic energy permits rapid dissolution of the powders in the liquid, which speeds up the overall acid-base reaction of the present invention. Once the paste has been mixed the working time of the paste of the present invention is about 5 minutes to about 15 minutes after the material has been mixed.

As the powder component is mixed with the liquid component, a number of reactions occur that begin the formation of the constituents of the final phosphosilicate of the present invention.

As known in the art, sparsely soluble silicates such as wollastonite, talc, and serpentine are slightly alkaline and when combined with water they become ionized, releasing the metal cations. For example, wollastonite dissolved in acidic water such as solutions of $H_3PO_4$, $KH_2PO_4$, $Al(H_2PO_4)_3$, etc, release cations $Ca^{+2}$ and silicate $SiO_3^{-2}$. The calcium cations react with phosphates to form calcium phosphates. The silicate anion formed metasilicic acid ($H_2SiO_3$), which further reacted with available cations to form $K_2SiO_3$ as seen in equation 5. Without wishing to be bound by theory, the formation of $CaHPO_4 \cdot 2H_2O$ is presumed to be brought about by the reaction represented by Equation 6 below.

$$CaSiO_3 \rightarrow Ca^{+2}(aq) + SiO_3^{-2} \quad \text{Equation 1}$$

$$H_3PO_4 \rightarrow 2H^+ + HPO_4^{-2} \quad \text{Equation 2}$$

$$2H^+ + SiO_3^{-2} \rightarrow H_2SiO_3 \quad \text{Equation 3}$$

$$Ca^{+2}(aq) + HPO_4^{-2} \rightarrow CaHPO_4 \quad \text{Equation 4}$$

$$2K^+ + H_2SiO_3 + 2OH^- \rightarrow K_2SiO_3 + 2H_2O \quad \text{Equation 5}$$

$$Ca^{+2}(aq) + HPO_4^{-2} + 2H_2O \rightarrow CaHPO_4 \cdot 2H_2O \quad \text{Equation 6}$$

Equation 1 and Equation 3 demonstrate that the addition of a sparsely soluble silicate such as calcium silicate produces metasilic acid. The metasilic acid reacts subsequently with other available cations, such as $2K^+$ as shown in equation 5 to form silicate glass. For example, if potassium dihydrogen phosphate was used instead of phosphoric acid water as the provider of phosphate anions, the metasilicic acid will react with either $K^+$ or $H^+$ to form alkali metal glass. This alkali metal glass formed within the phosphosilicate ceramic of the present invention is believed to fill the voids between the particles of the ceramic, and produces a dense solidified non-porous ceramic product. Additionally, the glassy phase within the ceramic product is also believed to bind particles of the product together to produce a strong ceramic, thus increasing both the compressive and flexural strength of the resulting product.

After the chemical reaction between the silicate and the binder, at least three products are produced, namely, magnesium potassium phosphate, $MgKPO_4 \cdot 6H_2O$, calcium hydrophosphate $CaHPO_4 \cdot 2H_2O$, and potassium silicate $K_2SiO_3$. The magnesium potassium phosphate provides the bulk strength for the new phosphosilicate ceramic, and the potassium silicate produces a glassy phase that fills the voids between the bulk compounds, resulting in a product that is almost completely dense. This glassy phase provides the benefits of reducing or even eliminating the porosity of the resulting ceramic and smoothing its surface.

In an optional embodiment, $Ca_4(PO_4)_2O$ (tetracalcium phosphate) can also be added to the reaction in order to form hydroxylapatite as a reaction product. Fukase et al., (Setting Reactions and Compressive Strengths of Calcium Phosphate Cements, in J. Dental Research, 69 (12), December 1990, pp. 1852–1856) has shown that hydroxylapatite phase can be synthesized by reacting $CaHPO_4$ with $Ca_4(PO_4)_2O$ by the reaction is set forth in Equation 7 below.

$$CaHPO_4 + Ca_4(PO_4)_2O \rightarrow Ca_5(PO_4)_3OH \quad \text{Equation 7}$$

The optional addition of $Ca_4(PO_4)_2O$ may be done by addition to the powder mixture, or by addition of $Ca_4(PO_4)_2O$ to the mixture of the powder component and the liquid component. The appropriate point in the process in which to add the $Ca_4(PO_4)_2O$ will depend on the pH of the liquid component, as the solubility of $Ca_4(PO_4)_2O$ varies with the pH of the solution into which the $Ca_4(PO_4)_2O$ is added. The amount of $CaHPO_4$ and $Ca_4(PO_4)_2O$ required will depend on the amount of $Ca_5(PO_4)_3OH$ desired. For example, if 25 weight percent $Ca_5(PO_4)_3OH$ is desired, but no $Ca_5(PO_4)_3OH$ is present in the initial powder, then the initial powder should comprises 6 percent by weight of $CaHPO_4$ and 19 percent by weight of $Ca_4(PO_4)_2O$. Human bones and teeth contain a high proportion of calcium phosphate compounds such as hydroxylapatite and other calcium phosphates. Retention of $Ca_5(PO_4)_3OH$ within the restorative material adds to the biocompatibility of the ceramic material of the present invention.

In addition, an alternative embodiment, namely those embodiments that include $Fe_2(HPO_4)_3$, $Fe_3(HPO_4)_4$, and/or $Bi_2(HPO_4)_3$, involves the creation of each compound's respective hydrophosphate phases, as set forth in Equations 8 through 10 below. While the colors of the hydrophosphate phases are not the same as the original oxide phases, only a small amount of the oxides react and form hydrophopsphates, which does not have a significant effect on the coloring provided by the oxides.

$$2Fe^{+3} + 3HPO_4^{-2} \rightarrow Fe_2(HPO_4)_3 \quad \text{Equation 8}$$

$$Fe^{+2} + 2Fe^{+3} + 4HPO_4^{-2} \rightarrow Fe_3(HPO_4)_4 \quad \text{Equation 9}$$

$$2Bi^{+3} + 3HPO_4^{-2} \rightarrow Bi_2(HPO_4)_3 \quad \text{Equation 10}$$

These hydrophosphates contribute to the mechanical properties of the final set material by enhancing the amount of the phosphate phase formed from the respective oxides.

In all of the investigations leading up to this invention, calcined MgO was a constituent of the substantially dry powder. In order to find the most appropriate calcination process for preparation of the powder used in the present invention, three different calcination processes were analyzed in an initial screening. Each of the three calcination processes had a different time/temperature profile, since the maximum soaking temperature in each of the three methods and the rate of both heating and cooling was different in all three methods. Partial calcination process time/temperature profiles can be seen in FIG. 1. The three different calcination processes are described in FIG. 1 as No. 01020702, No. 01020701, and No. 01020703. The best calcination process was discovered to be No. 01020702, which was calcined to about 1400° C. (2552° F.) and then cooled slowly over a period of about one day. This calcination process is distinct from the normal Ceramicrete calcination processes, which has a maximum calcination temperature of about 1300° C. (2370° F.). The calcination process listed as No. 01020701, heated up too much during setting. The calcination process listed as MgO—01020703 provided MgO that was acceptable to the material of the present invention, but the slurry of powders and liquid was too viscous.

Figure 2:
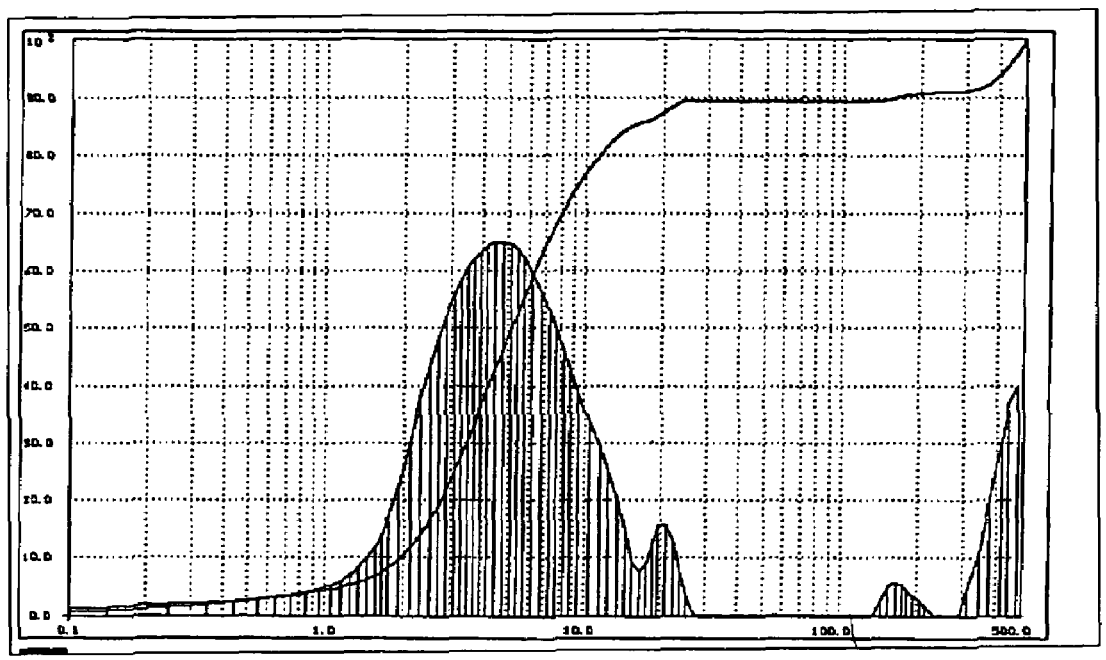
FIG. 2 is a particle size analysis of the hydroxylapatite used in the experiments of the present invention.

All of the MgO used for the following examples of this invention were sieved through 230 mesh for convenience, although the actual particle size was finer than 400 mesh (37 μm). All the other powders used were finer than 200 mesh (i.e. passed through 200 mesh screen (74 μm) and believed to be greater than 6 μm. In an optional embodiment, some of the powder component may be sieved through 325 mesh (44 μm). The particle size of the MgO is important because at feast some of the particles of MgO have to remain at least partially unreacted in order to act like nuclei for crystal growth. In addition, in all of the examples of the present invention used 10 grams of the substantially dry powder blend and were allowed to set for at least one day. All of the hydroxylapatite used in the following examples was also a very fine powder. The particle size of the hydroxylapatite was such that the mean particle size was about 5 μm. A particle size analysis of the present invention is included as FIG. 2. The darker line ascending from the left side of the graph of FIG. 2 to the right side shows the cumulative particle size with the axis on the left. The volume percentage for each of the particle size distribution channels is given as the area under the curve. The axis for this distribution is not shown but the maximum is less than 10 volume percent. Without wishing to be bound by theory, it is believed that the small size of the hydroxytapatite particles causes the hydroxylapatite to participate in the setting reaction of the present invention. Such participation is unusual because hydroxylapatite is a very unreactive material.

The material of the present invention may be used as a root canal sealer, a root canal obturation material, a root canal repair material such as for perforations, a material for apexification of root canals, a pulp-capping material, a temporary cement after root canal procedures, a temporary material after excavation of caries, temporary restorative material, a cement for a prosthodontic crown—either metal or ceramic, a cement for dental implants, a cement to replace or reimplant avulsed teeth, a dental ridge augmentation material to facilitate either dental implants or holding of a denture plate, periodontal defect filler, bone defect filler such as after an apicoectomy, bracket or band cement for orthodontics, pulp-capping material, coronal capping material for endodontics on top of an obturation material, cement for artificial joints such as replacement hips, knees or shoulders, a cement to stabilize broken or otherwise impaired bones, and/or a bone stabilizing cement. In addition, the viscosity of the material optionally may be adjusted by the addition of phosphate acids or soluble phosphates to fit an intended use in the body.

EXAMPLE 1. In a first example of the present invention, about 1 part by weight of a liquid was mixed with about 5 parts by weight of a substantially dry powder component to form the material of the present invention. The substantially dry powder component comprised about 12.5 weight percent MgO, about 38.5 weight percent $KH_2PO_4$, about 25 weight percent $CaSiO_3$, about 12.5 weight percent $CeO_2$, and about 12.5 weight percent $Ca_5(PO_4)_3OH$. The liquid component comprised about 11 weight percent $H_3PO_4$, and about 89 weight percent water. The powder component and the liquid component were mixed for about one minute and the mixture set in about 10 minutes. The final ceramic structure was substantially pore-free. A test of the compressive strength of the ceramic revealed that the compressive strength of the sample was about 14,000 psi. The set product had magnesium potassium phosphate hexahydrate as the bonding phase.

EXAMPLE 2. In a second example of the present invention, about 1 part by weight of a liquid component was mixed with about 1.875 parts by weight of a substantially dry powder component to form the material of the present invention. The substantially dry powder component comprised about 10.3 weight percent MgO, about 27.8 weight percent $KH_2PO_4$, about 41.2 weight percent $CaSiO_3$, about 10.3 weight percent $Bi_2O_3$, and about 12.5 weight percent $Ca_5(PO_4)_3OH$. The liquid component comprised about 50 weight percent $MgH_2PO_4.H_2O$, and about 50 weight percent water. To maximize the strength, the $MgH_2PO_4.H_2O$ was dissolved in the water prior to mixing the liquid with the other powders. The powder component and solution component was mixed for about two minutes. The paste had a working time of about 2.5 minutes. The compressive strength of the material in this example was found to be about 10,017±1162 psi after about 3 days. The density was 1.89 grams/cc and the open porosity was 2%. Hydrated phases, such as $MgKPO_4.6H_2O$ and $CaHPO_4.2H_2O$ formed hours after the setting of the paste, which strengthened the material.

EXAMPLE 3. In a third example of the present invention, about 1 part by weight of a liquid component was mixed with about 1.875 parts by weight of a substantially dry powder component to form the mixture of the present invention. The substantially dry powder component comprised about 10.3 weight percent MgO, about 27.8 weight percent $KH_2PO_4$, about 41.2 weight percent $CaSiO_3$, about 10.3 weight percent $CeO_2$, and about 12.5 weight percent $Ca_5(PO_4)_3OH$. The liquid component comprised about 50 weight percent $MgH_2PO_4.H_2O$, and about 50 weight percent water. The pH of the working paste was found to be about 4.34, which should not cause any acid-shock to the patient's pulp or other oral tissues. When the $MgH_2PO_4.H_2O$ was included in the powder mix, the strength of the final product was only about 900 psi, which is low for dental and orthopedic applications. To maximize the strength, the $MgH_2PO_4.H_2O$ was dissolved in the water prior to mixing the liquid with the other powders. The powder and solution was mixed for about two minutes. The paste had a working time of about 2.5 minutes. Hydrated phases, such as $MgKPO_{46}.6H_2O$ and $CaHPO_{42}.2H_2O$ formed hours after the working of the paste, strengthening the material. The compressive strength of the material in this example was found to be about 8,924±142 psi after about 3 days.

EXAMPLE 4. In a fourth example of the present invention, about 2.4 parts by weight of a liquid component was mixed with about 8 parts by weight of a substantially dry powder component to form the material of the present invention. The substantially dry powder component comprised about 1 part by weight MgO, about 3 parts by weight $KH_2PO_4$, about 2 parts by weight $CaSiO_3$, about 1 part by weight $CeO_2$, and about 1 part by weight $Ca_5(PO_4)_3OH$. The liquid component comprised about 11 weight percent $H_3PO_4$ and about 89 weight percent water. The powder and solution was mixed for about one minute and a thin paste was formed that set into a hard ceramic within about 5 minutes. Seven samples of this material were prepared and tested for compressive strength. At about three hours after setting, two samples of the material in this example were tested for compressive strength, which was found to be about 14,170±2,754 psi. At about one day after mixing, four samples of the material in this example were tested for compressive strength, which was found to be less variable but statistically the same, about 13,905±149 psi. At about seven days after setting, one sample of the material in this example was tested for compressive strength, which was found to be about 13,703 psi. Since this evidence shows that the full strength of the material is gained within the first three hours after mixing the material, the material is shown to be fast-setting, which makes such material good for dental application where the patient does not want to wait for an extended period of time for the material to gain such strength. The density of the example was found to be about 2.165 g/cm$^3$ and the open porosity volume was found to be about 0.77 percent of the total volume of the example. The open porosity could not be measured by mercury intrusion porosimetry, because the process of evacuation of pores removes bound water from the material, giving an error in the observation. The water immersion method of observation of open porosity was used instead, and the 0.77 percent open porosity measurement is within the error limit of the method, demonstrating that the open porosity volume could, in fact, be closer to about 0. This example proved to be the best compressive strength of all of the examples.

Figure 3:
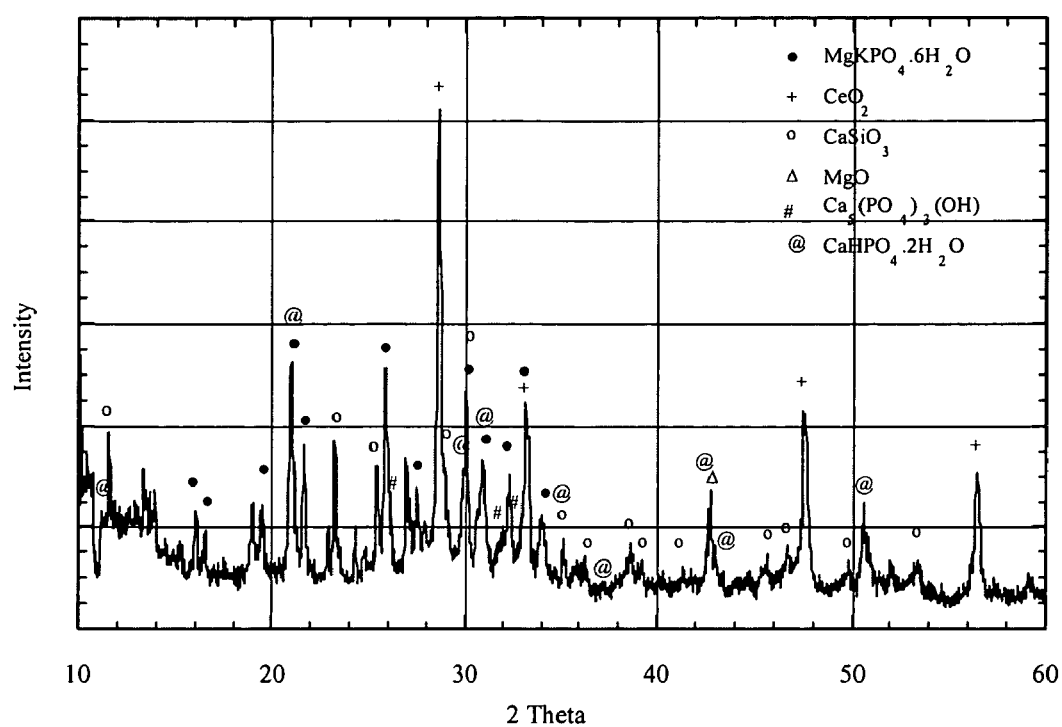
FIG. 3 is an x-ray diffraction analysis of an embodiment of the magnesium phosphate ceramic material of the present invention.
Figure 4:
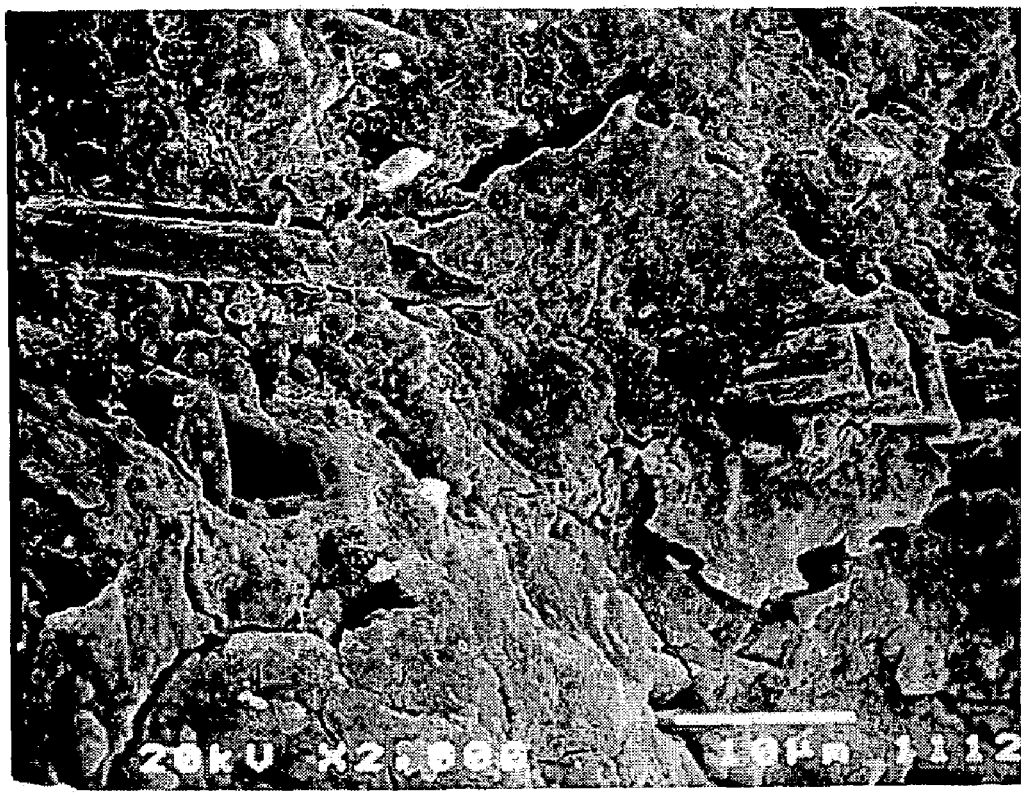
FIG. 4 is a scanning electron microphotograph of a sample of a fractured surface of a sample of an embodiment of the magnesium phosphate ceramic of the present invention.

The X-ray diffraction spectrum of this example is included as FIG. 3. FIG. 3 shows that, in addition to the expected phases, illustrated by very sharp peaks of $MgKPO_4.6H_2O$, unreacted $CeO_2$, unreacted $CaSiO_3$, unreacted MgO, and $Ca_5(PO_4)_3OH$, a new phase of $CaHPO_4.2H_2O$ has been observed. The $CaHPO_4.2H_2O$ phase is a biocompatible phase and makes this composition most suitable for dental or other biomaterials applications FIG. 4 is a scanning electron micrograph of the fracture surface of one of the samples. The photograph shows considerable amount of material that is featureless, possibly amorphous or microcrystalline. Due to the very fine powders used in this material, it is likely that crystals of $MgKPO_4.6H_2O$ formed within the material are very fine and hence are not easily visible in the micrograph. The only distinguishable feature in this photomicrograph are elongated crystals of $CaSiO_3$ that are embedded in this amorphous mass. The crack deflection around the elongated crystal is usually indicative of higher fracture toughness and also the elongated crystals themselves provide better flexural strength. FIG. 4 does not show any pores within the material. The lack of pores is visual evidence that the porosity of the material is probably about zero.

ADDITIONAL EXAMPLES. Twelve additional experiments were carried out during the investigation leading up to the invention. All of these experiments were carried out with a powder component comprising varied proportions of MgO, $KH_2PO_4$, $Ca_5(PO_4)_3OH$, $CeO_2$, and $CaSiO_3$ and a liquid component comprising water or an aqueous solution of $H_3PO_4$. Table 1, shown below includes the results from these investigations. The first three columns are the approximate numbers of parts of $Ca_5(PO_4)_3OH$, $CeO_2$, and $CaSiO_3$ on a weight basis. In all of the samples, the powder component comprises about 2 parts MgO by weight and about 2 parts $KH_2PO_4$ by weight in addition to the components set forth in Table 1. The fourth column is the concentration of $H_3PO_4$ in the liquid component. In the first row, the concentration of $H_3PO_4$ is zero because the liquid component used was only water.

TABLE 1

| Hydroxyl-apatite | $CeO_2$ | $CaSiO_3$ | Concentration of $H_3PO_4$ in solution | Number of parts of solution | One day Compressive strength (psi) |
|---|---|---|---|---|---|
| 0 | 0 | 0 | 0 | 2.2 | 1,055 |
| 0 | 0 | 0 | 11 | 2.4 | 4,180 |
| 0 | 0 | 2 | 11 | 2.4 | 9,275 |
| 1 | 0 | 0 | 11 | 2.4 | 7,793 |
| 1 | 1 | 0 | 11 | 2.4 | 9,834 |
| 0.5 | 1 | 2.5 | 5 | 2.4 | 10,075 |
| 0.5 | 1 | 2.5 | 5 | 2.8 | 6,650 |
| 1 | 1 | 2 | 5 | 2.4 | 6,927 |
| 1 | 1 | 2 | 5 | 2.8 | 9,685 |
| 1 | 1 | 2 | 11 | 2.8 | 12,375 |
| 0.5 | 1 | 2.5 | 11 | 2.4 | 12,450 |
| 0.5 | 1 | 2.5 | 11 | 2.8 | 8,313 |

The first row in Table 1 is an example of conventional fast-setting Ceramicrete without any additional additives. This example shows a relatively low compressive strength. The second row in Table 1 shows the conventional fast-setting Ceramicrete with $H_3PO_4$, which demonstrates about a four-fold increase in compressive strength over the conventional Ceramicrete composition. Without wishing to be bound by theory, it is believed that the addition of $H_3PO_4$ is responsible for the higher strength.

The third row in Table 1 is an example of conventional Ceramicrete, with $H_3PO_4$ and an addition 2 parts by weight $CaSiO_3$, which further enhanced the strength of the material. A similar strength enhancement was found when $Ca_5(PO_4)_3OH$ and $CeO_2$ were added, as shown in the fourth and fifth rows of Table 1. The samples in the subsequent rows demonstrate that the strength of the material is also enhanced over the basic Ceramicrete, when $CaSiO_3$, $Ca_5(PO_4)_3OH$, and $CeO_2$ were combined with $H_3PO_4$ using the conventional Ceramicrete components.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Histological tests were conducted using the ceramic material of the present invention 1 for pulp-capping in Class V cavities. The histology was determined after 33 and 120 days in sub-human primates (baboons). Large dentin bridges were formed indicating healing effect. Although the dentin formed was not as compact as desired, the results did indicate biocompatibility.

Additionally, a study was done in vitro to compare the setting of subject material to zinc phosphate cement. The study indicated that the strength to remove metal crowns from a tooth was the same for the traditional zinc phosphate cements as for the subject invention. However, the study also showed that the chemical durability of the ceramic composition of the subject invention is superior to that of zinc phosphate.

What is claimed is:

1. A mixture for forming a ceramic material for use in dental and orthopedic applications, the mixture comprising:
    about 65 percent to about 85 percent by weight of a substantially dry powder component, wherein the substantially dry powder component includes from about 5 percent to about 15 percent by weight of a sparsely soluble powder selected from the group consisting of a sparsely soluble oxide powder, a sparsely soluble hydroxide powder, and combinations thereof, from about 15 percent to about 45 percent by weight of a metal phosphate powder wherein the metal is selected from the group consisting of alkali metals, alkaline earth metals, group III metals, and combinations thereof, from about 15 percent to about 35 percent by weight of a sparsely soluble silicate powder, the balance of the substantially dry powder component comprising at least one powder selected from the group consisting of coloring powders, texturing powders, bioactive powders, biocompatible powders, fluorescent powders, fluoride releasing powders, and radiopaque powders;
    the balance of the mixture comprising a liquid component comprising a pH modifying agent in the range of about 5 percent by weight to about 15 percent by weight, up to about 60 percent of a monovalent alkali metal phosphate in aqueous solution, the balance of the liquid component being water; and
    wherein the pH of the mixture is above about 3.0, and wherein the sparsely soluble powder, metal phosphate powder, and sparsely soluble silicate powder each have a particle size of less than 20 μm.

2. The mixture of claim 1, wherein the sparsely soluble powder, metal phosphate powder, and sparsely soluble silicate powder collectively comprise about 75 weight percent of the substantially dry powder component.

3. The mixture of claim 1, wherein the sparsely soluble powder includes at least one of MyO, CaO, $ZrO_2$, $Zr(OH)_4$, FeO, $La_2O_3$, and $Al(OH)_3$.

4. The mixture of claim 1, wherein the metal phosphate powder includes at least one of $KH_2PO_4$, $NaH_2PO_4$, $Mg(H_2PO_4)_2$, and $Al(H_2PO_4)_3$.

5. The mixture of claim 4, wherein the metal phosphate powder is selected from the group consisting of: $KH_2PO_4$ at a molar ratio to MgO of about 1:1; $NaH_2PO_4$ at a molar ratio to MgO of about 1:1; $Mg(H_2PO_4)_2$ at a molar ratio to MgO of about 1:2; and $Al(H_2PO_4)_3$ at a molar ratio to MgO of about 1:3.

6. The mixture of claim 1, wherein the sparsely soluble silicate powder is at least one of $CaSiO_3$, $MgSiO_3$, $BaSiO_2$, and $Mg_3Si_2O_5(OH)_4$.

7. The mixture of claim 1, wherein the at least one powder selected from the group consisting of bioactive powders, biocompatible powders, fluorescent powders, fluoride releasing powders, and radiopaque powders includes at least one of $Ca_5(PO_4)_3OH$ and $Ca_4(PO_4)_2O$.

8. The mixture of claim 7, wherein the at least one powder comprises from about 5 percent to about 25 percent of the weight of the substantially dry powder component.

9. The mixture of claim 1, wherein the at least one powder selected from the group consisting of bioactive powders, biocompatible powders, fluorescent powders, fluoride releasing powders, and radiopaque powders includes at least one of a heavy metal compound selected from the group consisting of heavy metal oxides and heavy metal sulfates, fluoride containing compositions, and radiopaque glasses.

10. The mixture of claim 9, wherein the fluoride-containing composition is at least one of calcium fluoride, potassium fluoride, stannous fluoride, and fluoride-containing glass, the heavy metal compound is at least one of bismuth oxide, zinc oxide, lanthanum oxide, cerium oxide, terbium oxide, ytterbium oxide, neodymium oxide, zirconia, strontia, tin oxide, and barium sulfate, and wherein the radiopaque glasses is at least one of barium silicate, silico-alumino barium, and strontium-containing glass.

11. The mixture of claim 1, wherein the at least one powder selected from the group consisting of bioactive powders, biocompatible powders, fluorescent powders, fluoride releasing powders, and radiopaque powders includes at least one of a synthetic peptide-containing powder that enhances cell-binding with respect to collagen, and a calcium and phosphorus-containing glass that aids in regeneration of bone and periodontal tissue.

12. The mixture of claim 1, wherein the at least one powder selected from the group consisting of bioactive powders, biocompatible powders, fluorescent powders, fluoride releasing powders, and radiopaque powders includes a fluorescent powder that is selected from the group consisting of; fluorescent glass comprised of at least one lanthanide glass and oxides comprised of at least one lanthanide oxide.

13. The mixture of claim 12, wherein the lanthanide oxide is at least one of cerium oxide, praseodymium oxide, terbium oxide, erbium oxide, ytterbium oxide, and neodymium oxide.

14. The mixture of claim 1, wherein the at least one powder selected from the group consisting of coloring powders, texturing powders, bioactive powders, biocompatible powders, fluorescent powders, fluoride releasing powders, and radiopaque powders includes at least one of a non-hazardous metal oxide selected to provide coloring or texturing of the ceramic material upon setting.

15. The mixture of claim 14, wherein the non-hazardous metal oxide is at least one of $Al_2O_3$, $Al(OH)_3$, $Fe_3O_4$, $CeO_2$, and $Bl_2O_3$.

16. The mixture of claim 1, wherein the pH modifying agent is at least one of $H_3PO_4$ and $NH_4H_2PO_4$.

17. The mixture of claim 16, wherein the metal phosphate powder in aqueous solution is $MgH_2PO_4.H_2O$.

18. A mixture for forming a ceramic material for use in dental and orthopedic applications, the mixture comprising:
about 65 percent to about 85 percent by weight of a substantially dry powder component, wherein the substantially dry powder component includes from about 5 percent to about 15 percent by weight of calcined MgO, from about 15 percent to about 45 percent by weight of an alkali metal phosphate powder, from about 15 percent to about 35 percent by weight of $CaSiO_3$, from 0.5 percent by weight to about 25 percent by weight of $Ca_5(PO_4)_3OH$, the balance of the substantially dry powder component comprising at least one powder selected from the group consisting of bioactive powders, biocompatible powders) fluorescent powders, fluoride releasing powders, and radiopaque powders; and
the balance of the mixture comprising a liquid component comprising up to about 20 percent by weight of $H_3PO_4$, up to about 50 percent of $MgH_2PO_4.H_2O$, the balance of the liquid component being water.

19. A method of preparing a mixture for forming a ceramic material for use in dental and orthopedic applications, said method comprising the steps of:
providing a substantially dry powder component, said dry powder component comprising from about 5 percent to about 15 percent by weight of a sparsely soluble oxide powder, from about 15 percent to about 45 percent by weight of an alkali metal phosphate powder, from about 15 percent to about 35 percent by weight of a sparsely soluble silicate powder, the balance of the substantially dry powder component comprising at least one powder selected from the group consisting of bioactive powders, biocompatible powders, fluorescent powders, fluoride releasing powders, and radiopaque powders, said substantially dry powder component comprising about 65 percent to about 85 percent by weight of the mixture formed when the substantially dry component is combined with a liguid component;
providing a liquid component, said liquid component comprising from about 5 percent to about 15 percent by weight of a pH modifying agent, and from about 0 percent to about 50 percent of a monovalent alkali metal phosphate in aqueous solution, the balance being water;
mixing the substantially dry powder component with the liquid component to form a paste, wherein the pH of the paste is above about 3.0, and
wherein the step of providing a substantially dry powder component includes providing a sparsely soluble oxide powder comprising calcined MgO having a particle size of no greater than 37 μm.

20. The method of claim 19, wherein the MgO is calcined to about 1400degrees C. and then cooled slowly over a period of about 24 hours.

21. The mixture of claim 1, wherein the mixture is used for an orthopedic application.

22. The mixture of claim 1, wherein the mixture is used for a dental application.

23. A mixture for forming a ceramic material for use in dental and orthopedic applications, the mixture comprising:
about 65 percent to about 85 percent by weight of a substantially dry powder component, wherein the substantially dry powder component includes from about 5 percent to about 15 percent by weight of a sparsely soluble powder selected from the group consisting of a sparsely soluble oxide powder, a sparsely soluble hydroxide powder, and combinations thereof, from about 15 percent to about 45 percent by weight of a metal phosphate powder wherein the metal is selected from the group consisting or alkali metals, alkaline earth metals, group III metals, and combinations thereof, from about 15 percent to about 35 percent by weight of a sparsely soluble silicate powder, the balance of the substantially dry powder component comprising at least one powder selected from the group consisting of coloring powders, texturing powders, bioactive powders, biocompatible powders, fluorescent powders, fluoride releasing powders, and radiopaque powders;
the balance of the mixture comprising a liquid component comprising a pH modifying agent in the range of about 5 percent by weight to about 15 percent by weight, up to about 60 percent of a monovalent alkali metal phosphate in aqueous solution, the balance of the liquid component being water;
wherein the pH of the mixture is above about 3.0, and wherein the a sparsely soluble powder is comprised of MgO, CaO, $Zr(OH)_4$, and $Al(OH)_3$.

24. A mixture for forming a ceramic material for use in dental and orthopedic applications, the mixture comprising:
about 65 percent to about 85 percent by weight of a substantially dry powder component, wherein the substantially dry powder component includes from about 5 percent to about 15 percent by weight of a sparsely soluble powder selected from the group consisting of a sparsely soluble oxide powder, a sparsely soluble hydroxide powder, and combinations thereof, from about 15 percent to about 45 percent by weight of a metal phosphate powder wherein the metal is selected from the group consisting of alkali metals, alkaline earth metals, group III metals, and combinations thereof, from about 15 percent to about 35 percent by weight of a sparsely soluble silicate powder, the balance of the substantially dry powder component comprising at least one powder selected from the group consisting of coloring powders, texturing powders, bioactive powders, biocompatible powders, fluorescent powders, fluoride releasing powders, and radiopaque powders;
the balance of the mixture comprising a liquid component comprising a pH modifying agent in the range of about 5 percent by weight to about 15 percent by weight, up to about 60 percent of a monovalent alkali metal phosphate in aqueous solution, the balance of the liquid component being water;
wherein the pH of the mixture is above about 3.0, wherein the sparsely soluble silicate powder is at least one of $CaSiO_3$, $MgSiO_3$, $BaSiO_3$, and $Mg_3Si_2O_5(OH)_4$, and wherein the sparsely soluble silicate powder has a particle size of no greater than about 100 μm.

25. The mixture of claim 24, wherein the sparsely soluble silicate powder has a particle size of between about 1 μm to about 20 μm.

* * * * *

UNITED STATES PATENT AND TRADEMARK OFFICE
CERTIFICATE OF CORRECTION

| | | |
|---|---|---|
| PATENT NO. | : 7,083,672 B2 | Page 1 of 1 |
| APPLICATION NO. | : 10/913185 | |
| DATED | : August 1, 2006 | |
| INVENTOR(S) | : Wagh et al. | |

It is certified that error appears in the above-identified patent and that said Letters Patent is hereby corrected as shown below:

In column 1, line 45 "issued Oct. 17, 2000 issued Oct. 17, 2000;" should be -- issued October 17, 2000; --, In column 4, line 67 "working tim" should be -- working time --, In column 6, line 62 "soluble" should be -- "soluble oxide --, In column 7, line 8 "(FeO and/or $Fe_3O_4$," should be -- (FeO and/or $Fe_3O_4$), --, In column 7, line 63 "$Mg_{(H2PO42}$" should be -- $Mg(H_2PO_4)_2$--.

In column 11, line 29 "$^{k+}$" should be -- $K^+$ --.

In column 12, line 24 "$\rightarrow ^{Bi}_2(HPO_4)_3$" should be -- $\rightarrow Bi_2(HPO_4)_3$--, In column 14, line 24 "$MgKPO_{4.6.}6H_2O$" should be -- $MgKPO_4.6H_2O$ --, In column 17, line 20 "$BaSiO_2$," should be -- $BaSiO_3$, --, In column 17, line 59 "of;" should be -- of: --, In column 18, line 7 "$Bl_2O_3$." should be --$Bi_2O_3$. --, In column 18, line 25 "powders)" should be -- powders, --, In column 18, line 64 "1400degrees" should be -- 1400 degrees --.

Signed and Sealed this

Sixteenth Day of January, 2007

JON W. DUDAS
*Director of the United States Patent and Trademark Office*